(12) United States Patent
Prior et al.

(10) Patent No.: US 12,127,798 B2
(45) Date of Patent: Oct. 29, 2024

(54) UTERINE MANIPULATOR INCLUDING POSITION SENSOR

(71) Applicant: Covidien LP, Mansfield, MA (US)

(72) Inventors: Scott J. Prior, Branford, CT (US); Nikolai Begg, Wellesley, MA (US); Arvind Rajagopalan Mohan, Dracut, MA (US); Kevin R. Slisz, Old Saybrook, CT (US); Zachary Traina, Verona, NJ (US)

(73) Assignee: Covidien LP, Mansfield, MA (US)

( * ) Notice: Subject to any disclaimer, the term of this patent is extended or adjusted under 35 U.S.C. 154(b) by 819 days.

(21) Appl. No.: 17/192,532

(22) Filed: Mar. 4, 2021

(65) Prior Publication Data

US 2021/0275257 A1    Sep. 9, 2021

Related U.S. Application Data

(60) Provisional application No. 62/986,021, filed on Mar. 6, 2020.

(51) Int. Cl.
*A61B 34/20* (2016.01)
*A61B 5/00* (2006.01)
(Continued)

(52) U.S. Cl.
CPC ............ *A61B 34/20* (2016.02); *A61B 5/0051* (2013.01); *A61B 17/29* (2013.01); *A61B 17/4241* (2013.01); *A61B 34/35* (2016.02); *A61B 34/37* (2016.02); *A61B 90/39* (2016.02); *A61B 90/50* (2016.02); *A61B 2017/00287* (2013.01); *A61B 2017/00876* (2013.01); *A61B 2017/4225* (2013.01); *A61B 2034/2051* (2016.02); *A61B 2034/2059* (2016.02); *A61B 34/76* (2016.02); *A61B 2090/364* (2016.02); *A61B 2090/374* (2016.02); *A61B 2090/3762* (2016.02); *A61B 2090/3912* (2016.02); *A61B 2090/3937* (2016.02); *A61B 2090/3941* (2016.02); *A61B 2090/3945* (2016.02)

(58) Field of Classification Search
CPC ...... A61B 2090/395; A61B 2090/3945; A61B 2090/3941; A61B 2090/3937; A61B 2090/3912; A61B 2090/3762; A61B 2090/374; A61B 2090/364; A61B 2034/2059; A61B 2034/2051; A61B 2017/4225; A61B 2017/4216; A61B 2017/00907; A61B 2017/00876; A61B 2017/00557; A61B 2017/00287
See application file for complete search history.

(56) References Cited

U.S. PATENT DOCUMENTS 3,312,222 A    4/1967   Dwyer
3,938,521 A    2/1976   Ritota et al.
(Continued)

*Primary Examiner* — Jocelin C Tanner
(74) *Attorney, Agent, or Firm* — Carter, DeLuca & Farrell LLP

(57) ABSTRACT

A uterine manipulator includes a housing and a shaft extending distally from the housing. An end effector assembly is disposed at a distal end portion of the shaft. The end effector assembly includes a cervical cup and a uterine manipulating tip portion extending distally from the cervical cup. A position sensor is supported by the cervical cup. The position sensor is configured to identify a location of the cervical cup.

20 Claims, 7 Drawing Sheets

(51) Int. Cl.
*A61B 17/00* (2006.01)
*A61B 17/29* (2006.01)
*A61B 17/42* (2006.01)
*A61B 34/00* (2016.01)
*A61B 34/35* (2016.01)
*A61B 34/37* (2016.01)
*A61B 90/00* (2016.01)
*A61B 90/50* (2016.01)

(56) References Cited

U.S. PATENT DOCUMENTS

| | | |
|---|---|---|
| 5,643,285 A | 7/1997 | Rowden et al. |
| 5,645,083 A | 7/1997 | Essig et al. |
| 5,746,750 A | 5/1998 | Prestel et al. |
| 5,803,926 A | 9/1998 | Neward |
| 5,840,077 A | 11/1998 | Rowden et al. |
| 5,935,098 A | 8/1999 | Blaisdell et al. |
| 5,980,534 A | 11/1999 | Gimpelson |
| 7,717,312 B2 | 5/2010 | Beetel |
| 8,025,670 B2 | 9/2011 | Sharp et al. |
| 8,192,444 B2 | 6/2012 | Pycus |
| 8,292,901 B2 | 10/2012 | Auerbach et al. |
| 8,475,469 B2 | 7/2013 | Walter et al. |
| 8,603,105 B2 | 12/2013 | Sauer |
| 8,696,563 B2 | 4/2014 | Williams et al. |
| 8,740,916 B2 | 6/2014 | Blair et al. |
| 8,747,413 B2 | 6/2014 | Dycus |
| 9,011,433 B2 | 4/2015 | Batchelor et al. |
| 10,912,586 B2 | 2/2021 | Prior et al. |
| 2004/0152987 A1* | 8/2004 | Haisch ............... G01N 21/6458 600/476 |
| 2005/0277948 A1 | 12/2005 | Cedars et al. |
| 2010/0106163 A1 | 4/2010 | Blair et al. |
| 2010/0304333 A1 | 12/2010 | Ghavidel |
| 2011/0130769 A1 | 6/2011 | Boebel et al. |
| 2012/0109147 A1 | 5/2012 | Auerbach et al. |
| 2012/0330324 A1 | 12/2012 | Sauer |
| 2013/0023896 A1 | 1/2013 | Quimby |
| 2013/0138115 A1 | 5/2013 | Seckin |
| 2013/0345718 A1* | 12/2013 | Crawford ........... A61B 17/8866 606/130 |
| 2014/0052018 A1 | 2/2014 | Hawkins |
| 2014/0052144 A1 | 2/2014 | Singh et al. |
| 2014/0257322 A1 | 9/2014 | Batchelor et al. |
| 2014/0276812 A1 | 9/2014 | Batchelor |
| 2014/0288486 A1 | 9/2014 | Hart et al. |
| 2014/0330285 A1 | 11/2014 | Rosenblatt et al. |
| 2014/0358158 A1 | 12/2014 | Einarsson |
| 2015/0005780 A1 | 1/2015 | Einarsson |
| 2015/0127016 A1 | 5/2015 | Sauer |
| 2015/0133923 A1 | 5/2015 | Batchelor et al. |
| 2015/0148812 A1 | 5/2015 | Ahluwalia |
| 2015/0201964 A1* | 7/2015 | Murdeshwar ...... A61B 17/4241 600/37 |
| 2015/0272619 A1 | 10/2015 | Zisow |
| 2015/0297254 A1 | 10/2015 | Sullivan et al. |
| 2015/0351621 A1* | 12/2015 | Hill ........................ A61B 90/30 600/249 |
| 2016/0302783 A1 | 10/2016 | Greenberg et al. |
| 2017/0325844 A1 | 11/2017 | Prior |
| 2018/0325554 A1* | 11/2018 | Prior .................. A61B 17/4241 |
| 2019/0059948 A1 | 2/2019 | Kim et al. |
| 2019/0150983 A1 | 5/2019 | Prior et al. |
| 2020/0078109 A1* | 3/2020 | Steger .................... B25J 9/1697 |
| 2020/0229890 A1* | 7/2020 | Doyle ................... A61B 5/0086 |
| 2020/0253676 A1* | 8/2020 | Traina ..................... A61B 34/30 |
| 2020/0337729 A1 | 10/2020 | Begg et al. |
| 2021/0204910 A1* | 7/2021 | Begg .................... A61B 8/0841 |

* cited by examiner

UTERINE MANIPULATOR INCLUDING POSITION SENSOR

CROSS-REFERENCE TO RELATED APPLICATIONS

The present application claims the benefit of and priority to U.S. Provisional Patent Application No. 62/986,021, filed on Mar. 6, 2020, the entire content of which is incorporated by reference.

FIELD

The present disclosure relates to a uterine manipulator and, more particularly, to a uterine manipulator including a position sensor.

BACKGROUND

One of the final steps in a laparoscopic hysterectomy is a colpotomy, which requires making a circular incision in vaginal tissue to separate the uterus from the vagina. This incision is typically performed with the aid of a uterine manipulator. Uterine manipulators are conventionally used to position the vagina and the cervix to enable removal of the uterus or other tissue specimens after the colpotomy. Typically, uterine manipulators include a handle and a shaft extending distally from the handle that includes a cervical cup and an inflatable balloon. In use, the inflatable balloon is advanced through the vagina and cervix and is positioned within the uterus in a deflated position. Once positioned within the uterus, the inflatable balloon is inflated to secure the uterine manipulator within the uterus and the cervical cup is positioned about the cervix for effectuating the colpotomy.

During a colpotomy procedure, a sufficient distal force must be exerted on the uterine manipulator to mobilize the cervix away from the ureters such that the colpotomy incision can be performed. Applying insufficient force may allow the cervix to return to its anatomical position adjacent to the ureters, which may result in injury to the ureters during the colpotomy.

SUMMARY

In aspects of the disclosure, a uterine manipulator includes a housing and a shaft extending distally from the housing. An end effector assembly is disposed at a distal end portion of the shaft. The end effector assembly includes a cervical cup and a uterine manipulating tip portion extending distally from the cervical cup. A position sensor is supported by the cervical cup. The position sensor is configured to identify a location of the cervical cup.

In some aspects of the disclosure, at least one magnet is supported by the cervical cup as an alternative or in addition to the position sensor. The at least one magnet is configured to attract a metal surgical tool to identify the location of the cervical cup.

In some aspects of the disclosure, a vibrating element is supported by the cervical cup as an alternative or in addition to the position sensor and/or the at least one magnet. The vibrating element is configured to initiate ureter peristalsis.

In some aspects of the disclosure, a plurality of position sensors are arranged at a distal end portion of the cervical cup. The position sensors are arranged circumferentially around the distal end portion of the cervical cup.

In some aspects of the disclosure, the position sensors are arranged on a distal-facing surface of the cervical cup.

In some aspects of the disclosure, a fluorescent tag is supported by the cervical cup as an alternative or in addition to the position sensor, the at least one magnet, and/or the vibrating element. The fluorescent tag is configured to emit light to identify a location of the cervical cup.

In some aspects of the disclosure, the emitted light is non-visible to humans.

In some aspects of the disclosure, the fluorescent tag is supported on a distal-facing surface of the cervical cup.

In some aspects of the disclosure, the fluorescent tag is arranged circumferentially around a distal-end portion of the cervical cup.

In some aspects of the disclosure, the fluorescent tag is passively fluorescent.

In some aspects of the disclosure, the fluorescent tag is reactively fluorescent.

In some aspects of the disclosure, the fluorescent tag includes a power source configured to activate the fluorescent tag.

In aspects of the disclosure, a robotic system for operating a uterine manipulator includes at least one robot arm that operates the uterine manipulator. A display device displays images of a patient's anatomy overlaid with images of a position of the uterine manipulator relative to the patient's anatomy.

In some aspects of the disclosure, a pad includes a plurality of external position sensors. The pad is configured to be positioned under the patient. The pad is configured to detect a location of the position sensor supported by the cervical cup.

In some aspects of the disclosure, the images of the patient's anatomy are CT scan images.

In some aspects of the disclosure, a surgical grasping tool supports a second position sensor. The second position sensor is configured to identify a location of the surgical grasping tool.

In some aspects of the disclosure, a position sensing scope is configured to detect a position of the positon sensor supported by the cervical cup.

Other features of the disclosure will be appreciated from the following description.

BRIEF DESCRIPTION OF THE DRAWINGS

The accompanying drawings, which are incorporated in and constitute a part of this specification, illustrate aspects and features of the disclosure and, together with the detailed description below, serve to further explain the disclosure, in which.

DETAILED DESCRIPTION

Figure 1:
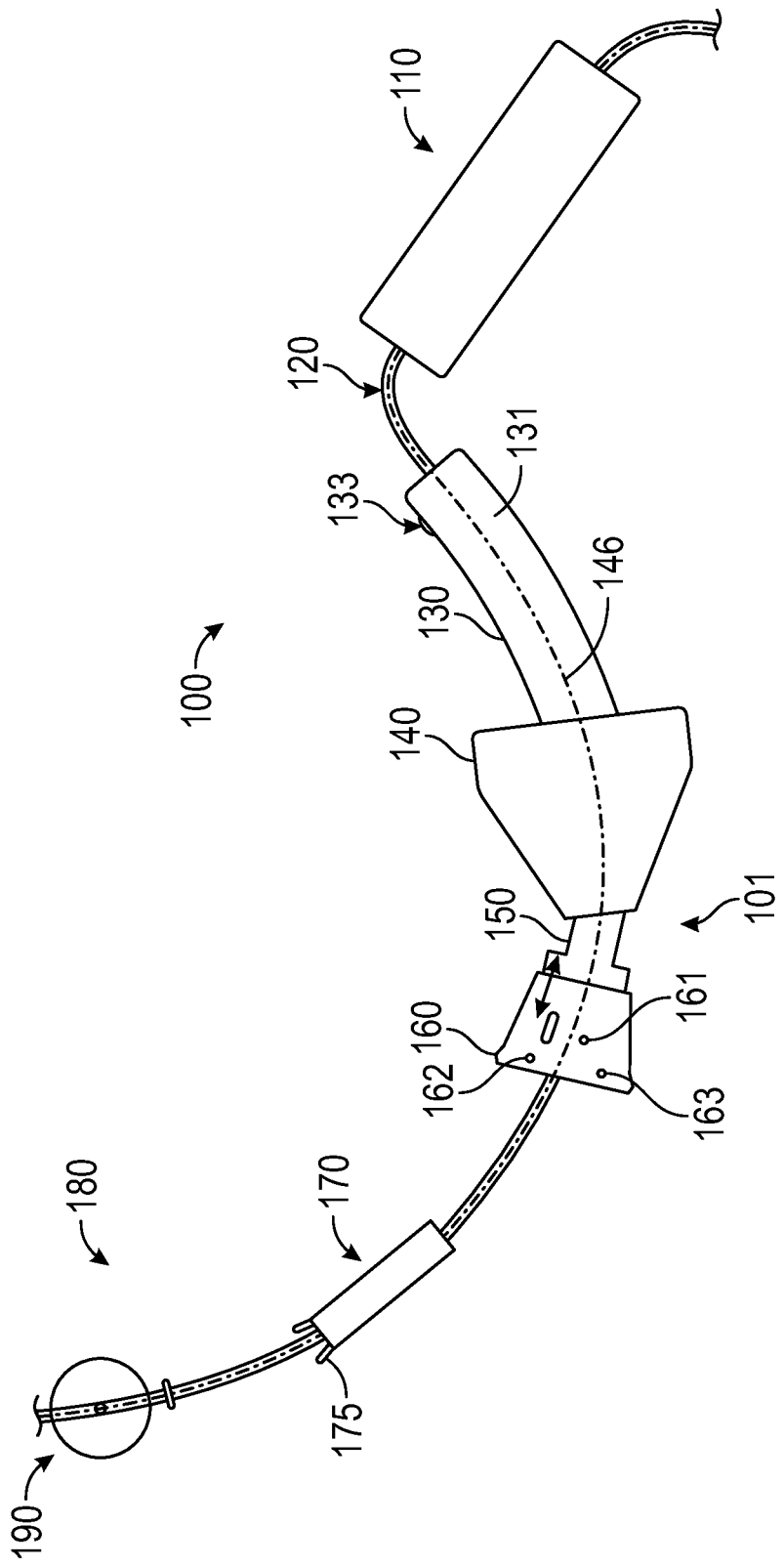
FIG. 1 is a side view of a uterine manipulator in accordance with the aspects and features of present disclosure.

During procedures employing a uterine manipulator (UM), a surgeon may rely on visual cues of anatomy to ascertain where in the UM is positioned with respect to a patient's anatomy. When visual cues cannot be used, the surgeon may rely on tactile feedback between a laparoscopic tool and the UM to determine if the UM is in a desired location (e.g., with a cervical cup of the UM engaged with the patient's cervix). According to aspects of the present disclosure, position sensors are utilized to determine a location of the UM within the anatomy of the patient. Position sensors may be used to identify a location of laparoscopic tools, a cervical cup, and any other element of the UM. The locations of each of the above-noted elements can be overlaid with CT scan or MRI images of the patient's anatomy in real-time as a single image or video feed on a display. Additionally, electromagnetic navigation and/or fluoroscopic imaging can be employed to assist with navigating the UM to a desired position and/or manipulating the UM in order to perform a surgical task, e.g., a colpotomy.

As used herein, the term "distal" refers to the portion that is being described which is farther from a user, while the term "proximal" refers to the portion that is being described which is closer to a user. Further, to the extent consistent, any of the aspects and features detailed herein may be used in conjunction with any or all of the other aspects and features detailed herein.

Exemplary axes or directions such as an X-axis direction, a Y-axis direction and a Z-axis direction may be illustrated in the accompanying drawings and/or described herein. As an example, the X-axis direction may be perpendicular to the Y-axis direction, and the Z-axis direction may be orthogonal to the X-axis direction and the Y-axis direction.

Descriptions of technical features or aspects of an exemplary embodiment of the disclosure should typically be considered as available and applicable to other similar features or aspects in another exemplary embodiment of the disclosure. Accordingly, technical features described herein according to one exemplary embodiment of the disclosure may be applicable to other exemplary embodiments of the disclosure, and thus duplicative descriptions may be omitted herein.

Aspects of the disclosure will be described more fully below (e.g., with reference to the accompanying drawings). Like reference numerals may refer to like elements throughout the specification and drawings.

Referring to FIGS. 1-4, a uterine manipulator is shown and generally identified by reference numeral 100. Uterine manipulator 100 is generally configured for insertion through the vaginal cavity "V" and into the uterus "U" and is used to mobilize and/or position the uterus "U" during surgical procedures (see FIGS. 2-4). Uterine manipulator 100 generally includes a housing 110 and a shaft 120 extending from housing 110. The housing 110 may include a handle configured for human operation of the uterine manipulator 100, or the housing 110 may be secured to a robotic arm for robotic operation of the uterine manipulator 100. In some aspects, shaft 120 supports one or more of a slidable occluder shaft 130, an occluder 140, a shuttle 150, a cervical cup 160, a specimen containment system 170, and a uterine manipulating tip portion 180 including an inflatable balloon 190. Depending upon the desired configuration, uterine manipulator 100 may include some or all of these features or may include additional or alternative features suitable for use with a uterine manipulator 100.

Figure 2:
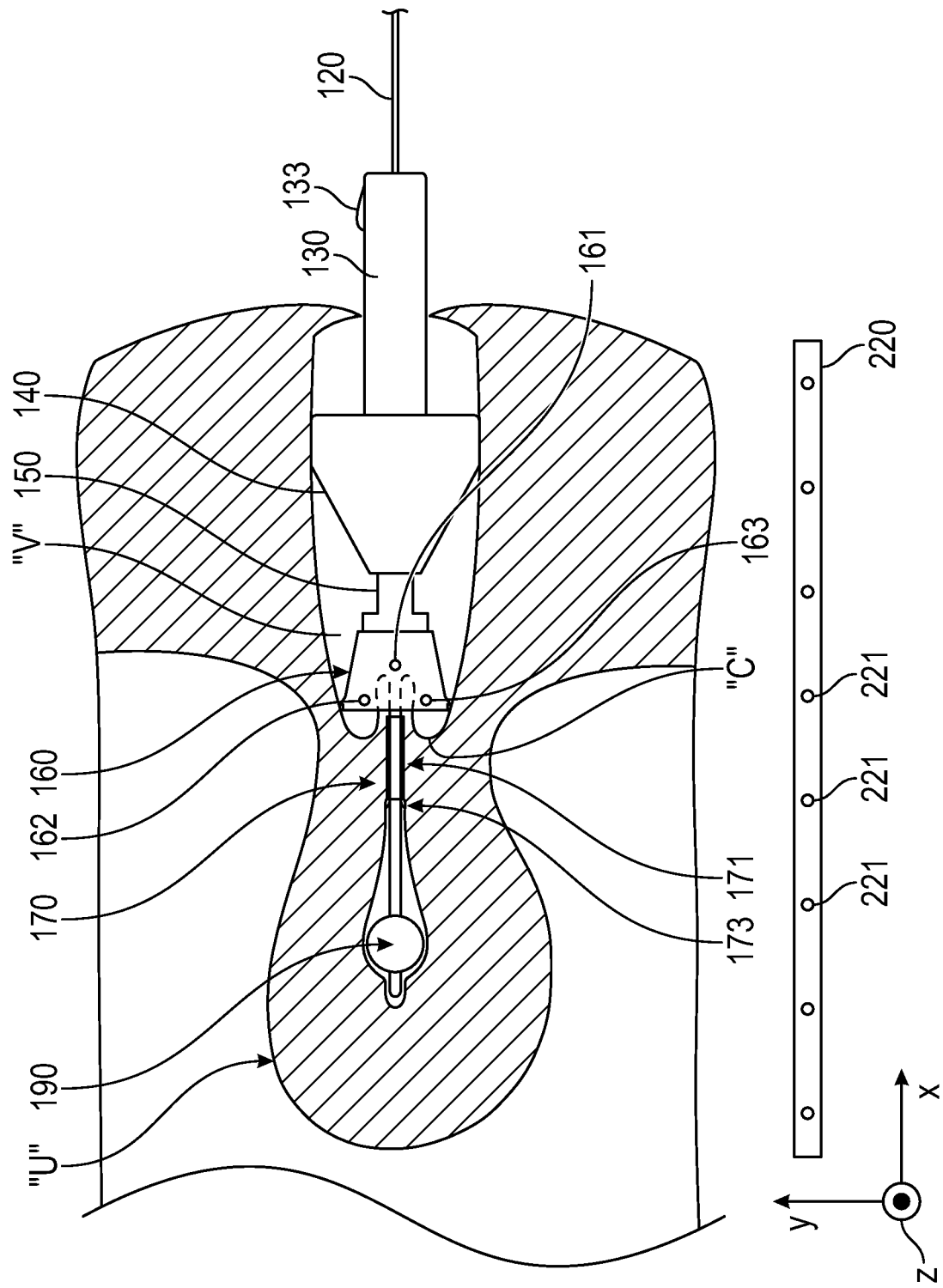
FIG. 2 is a schematic diagram of a distal end portion of the uterine manipulator of FIG. 1 disposed within a vaginal cavity of a patient and engaged with a cervix of the patient.
Figure 3:
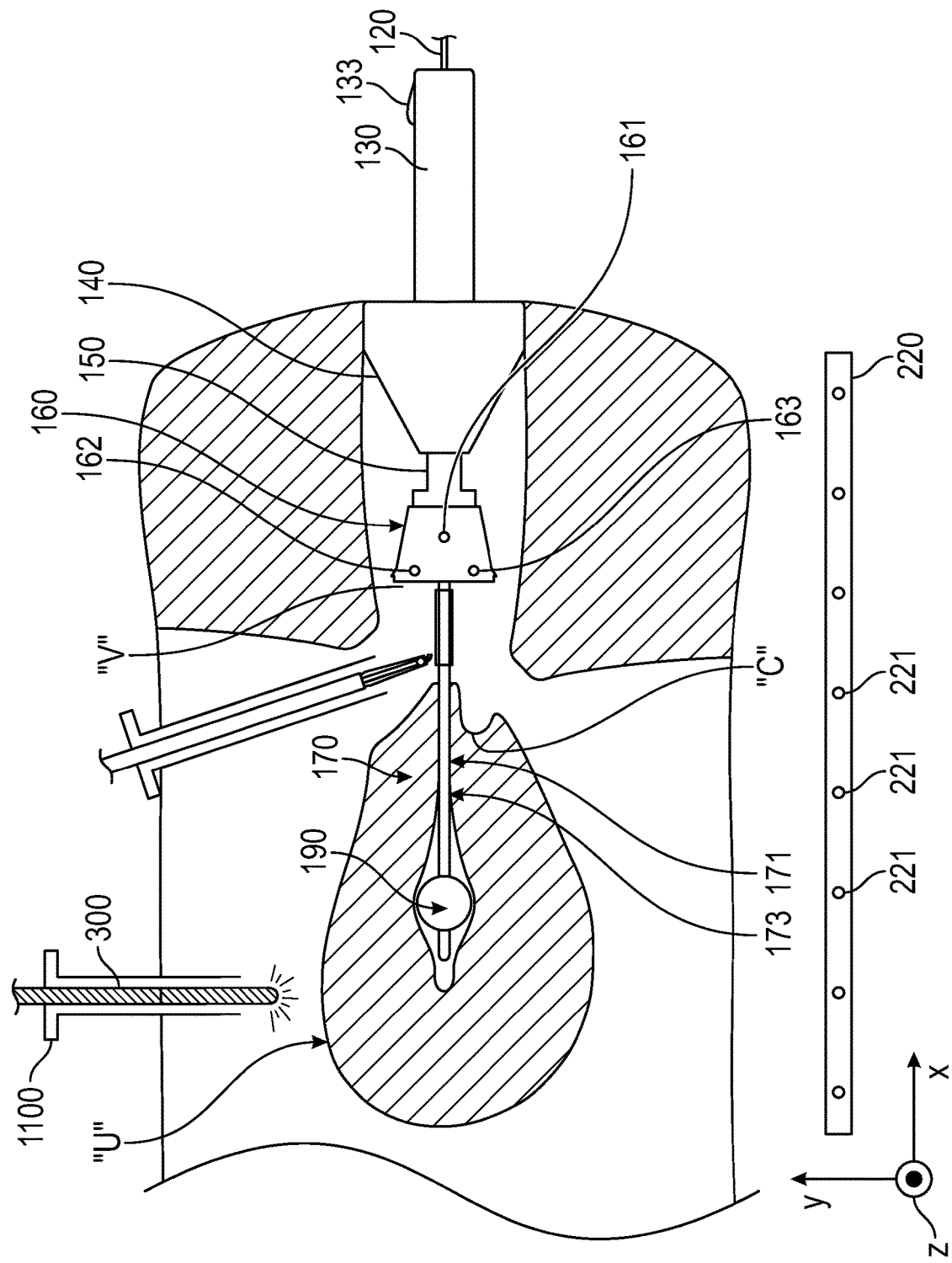
FIG. 3 is a schematic diagram of the distal end portion of the uterine manipulator of FIG. 2 disposed within the vaginal cavity and a surgical grasping tool inserted adjacent the cervix of the patient.
Figure 4:
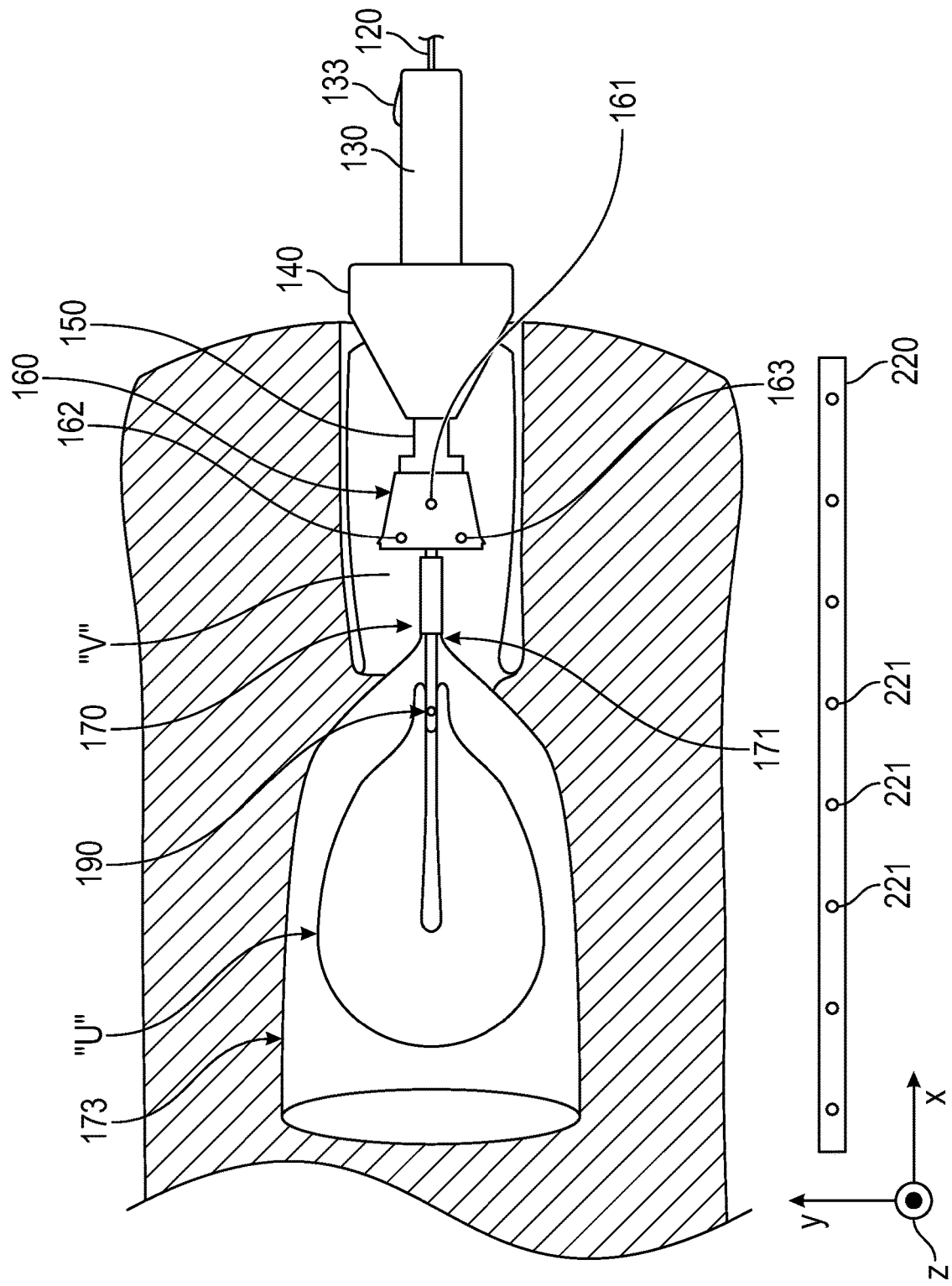
FIG. 4 is a schematic diagram of the distal end portion of the uterine manipulator of FIG. 3 disposed within the vaginal cavity with a specimen bag in a deployed position around a transected uterus.

Housing 110 of uterine manipulator 100 is configured to enable gripping and manipulation of uterine manipulator 100 (e.g. by a human hand or a robotic arm). Movement (e.g., axial, pivoting, rotation, etc.) of housing 110 causes uterine manipulating tip portion 180 to move for moving and/or positioning the uterus "U" (FIGS. 2-4), for example, for retroversion and anteversion of the uterus "U" (FIGS. 2-4).

In one aspect, at least one position sensor 161 is supported by the cervical cup 160. The position sensor 161 is configured to identify a location of the cervical cup 160. As an example, the at least one position sensor 161 may be supported at a distal end portion of the cervical cup 160. However, multiple positon sensors 161 may be arranged at various locations about the cervical cup 160. For example, a first position sensor 161 may be arranged at a proximal end portion of the cervical cup 160 while a second position sensor 161 is arranged at the distal end portion of the cervical cup 161. Multiple position sensors 161 spaced-apart on the cervical cup 160 enable triangulation and, thus, three-dimensional position and orientation determination for the cervical cup 160.

In some aspects, at least one magnet 162 is supported by the cervical cup 160. The at least one magnet 162 is configured to attract a metal surgical tool (e.g., grasping device 200 of FIG. 3) to identify the location of the cervical cup 160. When the metal surgical tool is in relatively close proximity to the at least one magnet 162, an operator of the metal surgical tool may feel the attractive force between the metal surgical tool and the at least one magnet 162. This can be used to confirm that the cervical cup 160 supporting the at least one magnet 162 is in a desired location (e.g., engaged with the patient's cervix "C") and/or that the metal surgical tool is in proper position relative to the cervical cup 160.

In some aspects, a vibrating element 163 is supported by the cervical cup 160. The vibrating element 163 is configured to initiate ureter peristalsis. The occurrence of ureter peristalsis can be used to confirm that the cervical cup 160 is in contact with a ureter of the patient to determine a location of the cervical cup 160.

Figure 5:
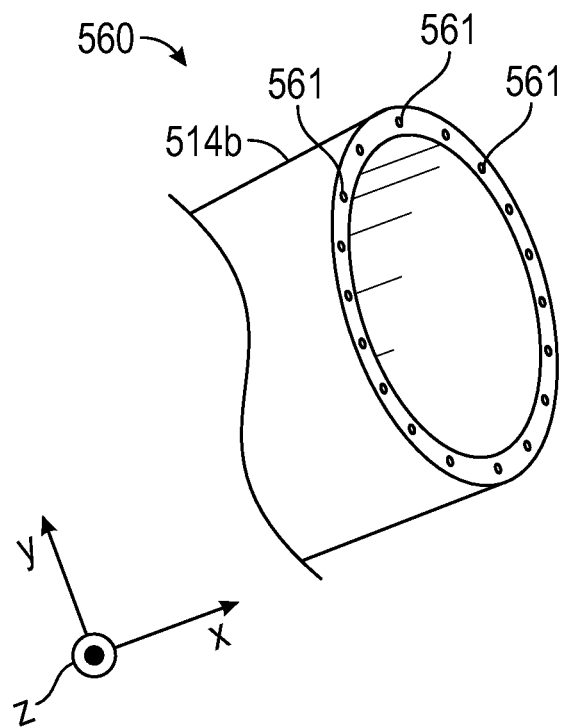
FIG. 5 is a perspective view of a cervical cup supporting positon sensors in accordance with the aspects and features of present disclosure.

Referring to FIG. 5, a plurality of position sensors 561 are arranged at a distal end portion 514b of the cervical cup 560. The position sensors 561 are arranged circumferentially around the distal end portion 514b of the cervical cup 560, e.g., about an outwardly-facing surface thereof. The position sensors 561 may be intermittently spaced apart from each other around the distal end portion 514b of the cervical cup 560. This allows visualization of a directional orientation of the distal end portion 514b of the cervical cup 560 to determine if the cervical cup 560 is engaged with the patient's cervix "C" or otherwise positioned.

Figure 6:
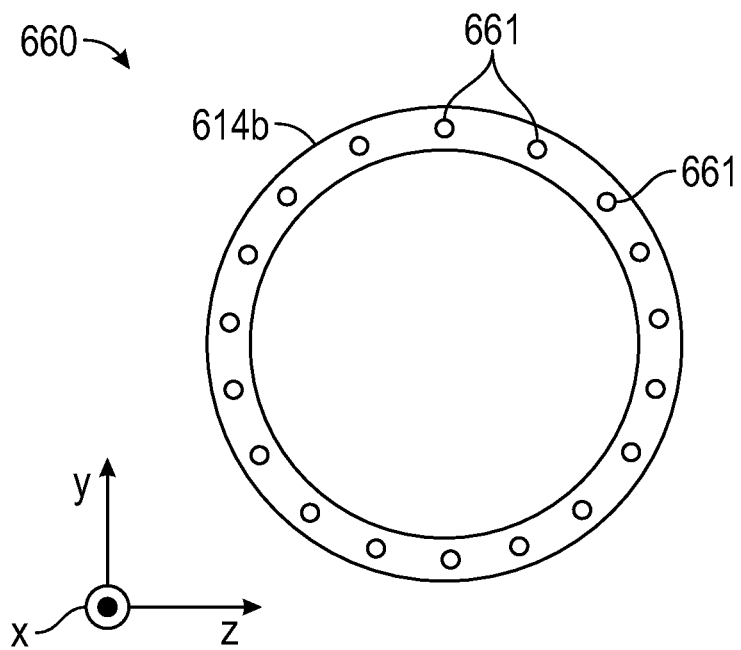
FIG. 6 is an end view of another cervical cup supporting position sensors in accordance with the aspects and features of present disclosure.

Referring to FIG. 6, a plurality of positon sensors 661 are arranged on a distal-facing surface 614b of the cervical cup 660, e.g., about an distal rim thereof. The position sensors 661 may be intermittently spaced apart from each other and arranged circumferentially around the distal facing surface 614b of the cervical cup 660.

Figure 7:
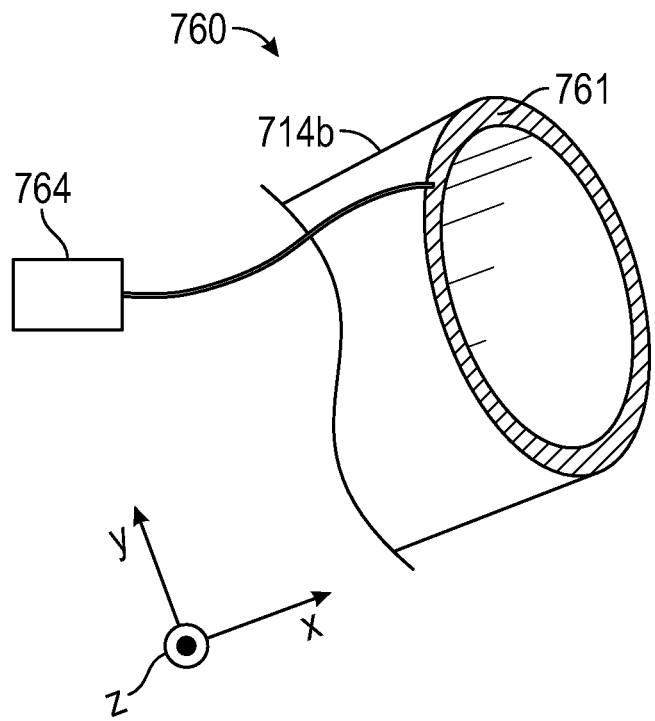
FIG. 7 is a perspective view of a cervical cup supporting a fluorescent tag in accordance with the aspects and features of present disclosure.
Figure 8:
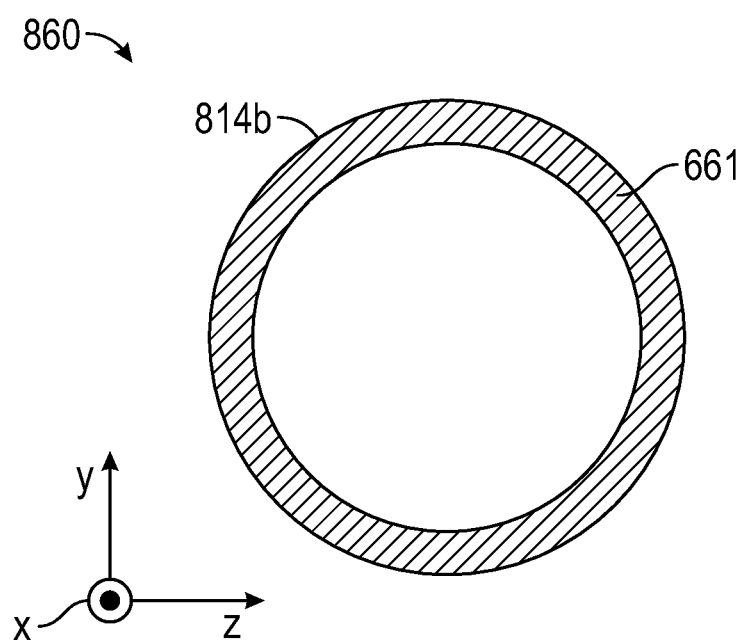
FIG. 8 is an end view of another cervical cup supporting a fluorescent tag in accordance with the aspects and features of present disclosure.

Referring to FIGS. 7 and 8, cervical cups 760, 860 support fluorescent tags 761, 861, respectively. The fluorescent tags 761, 861 are configured to emit light (e.g., light non-visible to humans) to identify a location of the cervical cups 760, 860.

The fluorescent tags 761, 861 of cervical cups 760, 860 may be passively fluorescent. For example, a distal end portion 714b (FIG. 7) or a distal-facing surface 814b (FIG. 8) of the cervical cups 760, 780, respectively, includes a material with fluorescent properties. The material may be a polymer impregnated with one or more fluorescent agents or a fluorescent agent may be applied as a surface treatment. When non-visible light from a surgical imaging system excites the fluorescent agent, the fluorescent agent fluoresces and is visible by a surgical imaging system. The fluorescent agent may be visible through tissue, and thus emitted light may be detected across a patient's cervix, such as by a position sensing scope 300 (FIG. 3). The position sensing scope 300 (FIG. 3) may be a camera configured to detect a corresponding wavelength of light emitted by the fluorescent agent.

The cervical cups 760, 860 may be reactively fluorescent. For example, a reaction occurs before or during a surgical procedure that causes the fluorescent agent to emit light (e.g., non-visible light to humans) without excitation from a surgical system. As an example, an external light source may emit light onto the cervical cups 760, 860 to activate the fluorescent agent.

The cervical cups 760, 860 may include a chamber with multiple chemical agents not in direct contact with each other in a first configuration, and when agitated or otherwise mixed the chemical agents combine to react and emit light.

The cervical cups 760, 860 may include a temperature-activated fluorescent agent that emits light when placed in contact with a patient's body to expose the fluorescent agent to physiological temperatures.

The cervical cups 760, 860 may include an air-activated fluorescent agent. In a first configuration, the air-activated fluorescent agent is covered, and in a second configuration the air-activated fluorescent agent is exposed to air to cause the air-activated fluorescent agent to emit light.

The cervical cups 760, 860 may include a water-activated or saline-activated fluorescent agent.

The cervical cups 760, 860 may include a fluorescent agent activated by a power source 764 (e.g., a battery).

As an example, the cervical cups 760, 860 may be coated with indocyanine green (ICG) dye for use with fluoroscopic imaging of the cervical cups 760, 860. Infrared (IR) light of a predetermined wavelength (e.g., 785 nm) may be employed for activating the ICG dye to visualize a position of the instrument (e.g., via an infrared camera inserted through the first access cannula 1100 (FIG. 3)).

Referring particularly to FIG. 7, the fluorescent tag 761 is supported on a distal-end portion 714b of the cervical cup 760. The fluorescent tag 761 may extend circumferentially around an outwardly-facing surface at the distal-end portion 714b.

Referring particularly to FIG. 8, the fluorescent tag 861 is arranged circumferentially around a distal-facing portion 814b of the cervical cup 860.

Figure 9:
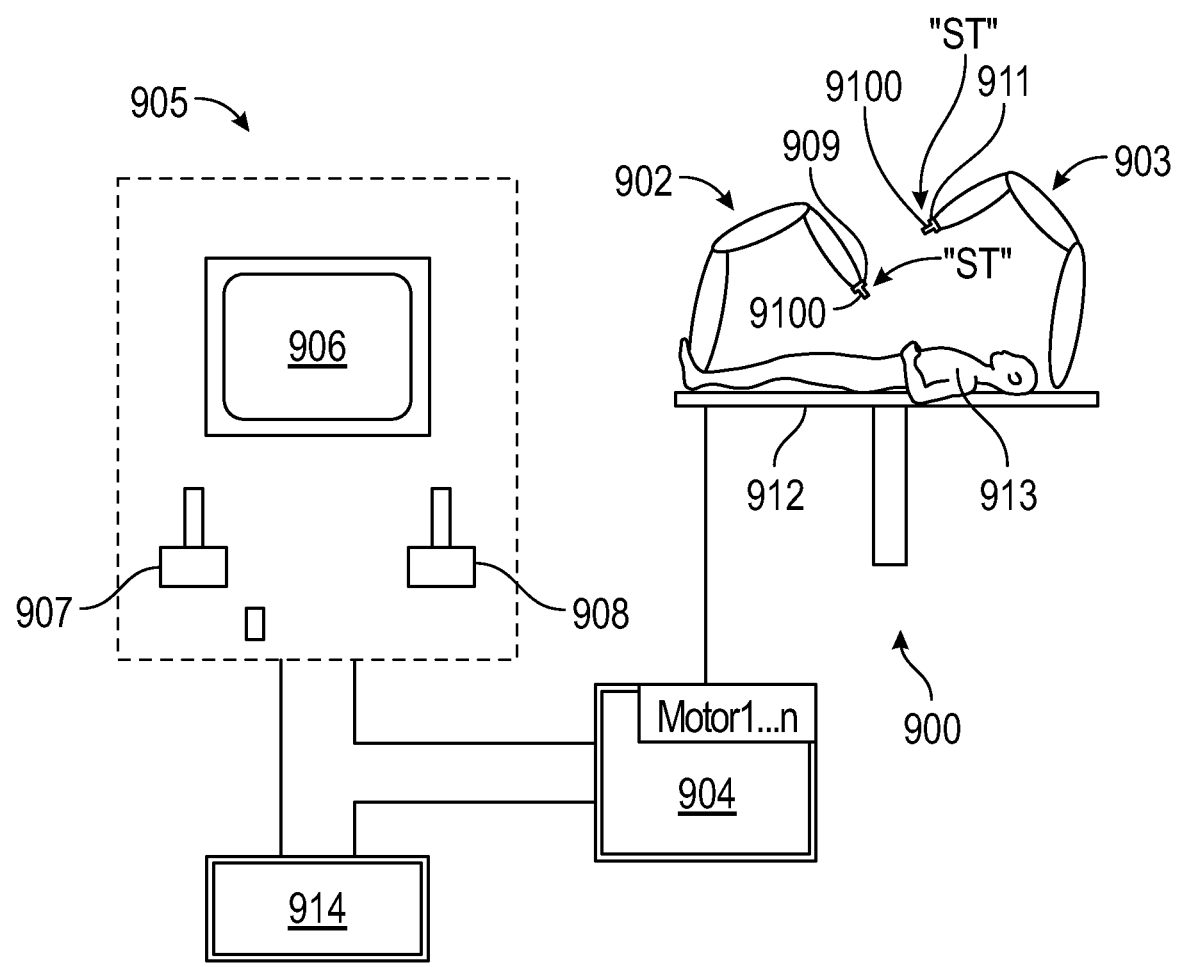
FIG. 9 is a schematic illustration of a robotic surgical system configured for use in accordance with the present disclosure.

FIG. 9 illustrates a robotic surgical system shown generally as system 900 and generally may include a plurality of robot arms 902, 903 configured to operate surgical tools "ST"; a control device 904; and an operating console 905 coupled with control device 904. Operating console 905 may include a display device 906, which may be set up in particular to display three-dimensional images; and manual input devices 907, 908, by means of which a person (not shown), for example a surgeon, may be able to telemanipulate robot arms 902, 903 in a first operating mode.

Each of the robot arms 902, 903 may include a plurality of members, which are connected through joints, and an attaching device 909, 911, to which may be attached, for example, the surgical tool "ST" supporting an end effector 9100, e.g., uterine manipulator 100 (FIG. 1) and the end effector components thereof.

Robot arms 902, 903 may be driven by electric drives (not shown) that are connected to control device 904. Control device 904 (e.g., a computer) may be set up to activate the drives, in particular by means of a computer program, in such a way that robot arms 902, 903, their attaching devices 909, 911 and thus the surgical tool "ST" (including end effector 9100) execute a desired movement according to a movement defined by means of manual input devices 907, 908. Control device 904 may also be set up in such a way that it regulates the movement of robot arms 902, 903 and/or of the drives.

System 900 may be configured for use on a patient 913 lying on a patient table 912 to be treated in a minimally invasive manner by means of end effector 9100. System 900 may also include more than two robot arms 902, 903, the additional robot arms likewise being connected to control device 904 and being telemanipulatable by means of operating console 905. A medical instrument or surgical tool "ST" (including an end effector 9100) may also be attached to the additional robot arm. System 900 may include a database 914, in particular coupled to with control device 904, in which are stored, for example, pre-operative data from patient/living being 913 and/or anatomical atlases.

Referring to FIGS. 1-4 and 9, a robotic system for operating the uterine manipulator 100, more specifically, includes the system 900 including the control device 904 and plurality of robot arms 902, 903. The robot arms 902, 903 can be employed to operate the uterine manipulator 100. The display device 906 displays images of a patient's anatomy overlaid with images of a position of the uterine manipulator 100 relative to the patient's anatomy. The images of the patient's anatomy may be derived from computed tomography (CT) images, magnetic resonance imaging (MRI) images, and/or fluoroscopic images.

In some aspects, a reference pad 220 (FIGS. 2-4) includes a plurality of external position sensors 221 configured to generate an electromagnetic field. The reference pad 221 is configured to be positioned under the patient. The reference pad 221 is configured to detect a location of the position sensors (e.g., sensors 161) supported by the cervical cup (e.g., cervical cup 160) and/or any other position sensor(s) within the field of the reference pad 220 (e.g., position sensor 211 at a distal end of surgical grasping device 200). The reference pad 220 may be an electromagnetic filed transmitter positioned beneath the patient such that positions of any position sensors within the electromagnetic field can be determined by the reference pad 220.

In some aspects, navigation of the medical instruments described herein is achieved by use of an electromagnetic navigation (EMN) system. In general, the EMN system is configured to identify a location and/or an orientation of a medical device being navigated toward a target location within the patient's body by using, among other things, an antenna assembly that generates one or more electromagnetic fields that are sensed by a sensor affixed to the medical device. In some cases, the EMN system is further configured to augment computed tomography (CT) images, magnetic resonance imaging (MRI) images, and/or fluoroscopic images employed during navigation of the medical device through the patient's body toward a target of interest.

Referring again to FIG. 3, the first access cannula 1100 may be inserted into the uterus "U" and the position sensing scope 300 may be inserted through the first access cannula 1100. The position sensing scope 300 may emit a signal (e.g., an audio signal or an infrared signal) to any of the position sensors described herein and receives a reply signal useable for determining the position of the position sensor. A second access cannula 2100 may be inserted into the vagina "V" and the surgical grasping device 200 may be inserted through the second access cannula 2100. Alternatively, each of the first access cannula 1100 and the second access cannula 2100 may be inserted into the uterus "U."

Referring again to FIGS. 1-4, in some aspects, uterine manipulator 100 includes specimen containment system 170 or other deployable system incorporated thereon. Specimen containment system 170 includes a sleeve 171 supported on shaft 120 of uterine manipulator 100. Sleeve 171 generally defines an elongate tubular shape and is configured to extend through the vaginal cavity "V" (FIGS. 2-4). Sleeve 171 may be movable along shaft 120 or may be fixed relative thereto. Sleeve 171 may be formed from any suitable material such as stainless steel, plastic, titanium, or the like.

A specimen containment bag 173 is disposed within sleeve 171. Specimen containment bag 173 may be formed from any suitable material. In particular, specimen containment bag 173 may be formed from a transparent, tear-resistant, and/or stretchable material to enable visualization into specimen containment bag 173 from the exterior thereof, inhibit tearing, and/or facilitate manipulation of specimen containment bag 173, tissue specimen(s), and/or surgical instrumentation during use.

With the uterus "U" separated from the vagina "V," e.g., after performing a colpotomy, the uterine manipulator 100 may be positioned such that the specimen containment system 170 is located proximally of the uterus "U." The clinician may then insert a grasping device 200 including a pair of jaws 210 through a separate port or incision (FIG. 3) to grasp and pull the rim 175 of the specimen containment bag 173 out of the sleeve 171 such that the specimen containment bag 173 moves from the initial position (FIG. 3) to the deployed position (FIG. 4) to surround the uterus "U." Additionally or alternatively, housing 110 may be manipulated to move shaft 120 proximally and/or distally such that the uterus "U" provides counter-traction against the specimen containment system 170 to cause specimen bag 173 of specimen containment system 170 to deploy from sleeve 171. Rim 175 of specimen containment bag 173 causes specimen containment bag 173 to expand outwardly once removed or deployed from sleeve 171. As an alternative to manual deployment, an actuation shaft (not shown) may be translated relative to shaft 120, specimen containment bag 173, and/or sleeve 171 to deploy specimen containment bag 173 therefrom, as noted above.

Once the specimen containment bag 173 is deployed above the uterus "U," uterine manipulator 100 may be withdrawn from the vaginal cavity "V," leaving specimen containment bag 173 in place around the transected uterus "U." Alternatively, in aspects where sleeve 171 is fixedly attached to specimen bag 173, the combination of sleeve 171 and specimen bag 173 may remain in the vaginal cavity "V" as the remainder of the uterine manipulator 100 is withdrawn from the vaginal cavity "V." One or both ends of the specimen containment bag 173 may then be closed and/or externalized. The transected uterus "U" can then be morcellated from within the specimen containment bag 173, if needed, and remaining end(s) of the specimen containment bag 173 may then be closed and/or externalized. Because the tissue specimen is contained within the specimen bag 173 during morcellation, the seeding of cancer cells is prevented. Finally, the specimen containment bag 173 is removed. As can be appreciated, the various sensors, magnets, and/or tags detailed herein may be utilized to facilitate the colpotomy, containment, morcellation, and/or extraction detailed above, or any other suitable surgical task, using containment system 170 disposed on the uterine manipulator 100 as detailed above or using any other suitable instruments/systems coupled to or separate from uterine manipulator 100.

From the foregoing and with reference to the various figure drawings, those skilled in the art will appreciate that certain modifications can also be made to the disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A uterine manipulator, comprising:
   a housing;
   a shaft extending distally from the housing;
   an end effector assembly disposed at a distal end portion of the shaft, the end effector assembly including a cervical cup and a uterine manipulating tip portion extending distally from the cervical cup;
   a position sensor supported by the cervical cup, the position sensor configured to identify a location of the cervical cup; and
   at least one magnet supported by the cervical cup, the at least one magnet configured to attract a metal surgical tool to identify the location of the cervical cup.

2. The uterine manipulator of claim 1, further including a vibrating element supported by the cervical cup, the vibrating element configured to initiate ureter peristalsis.

3. The uterine manipulator of claim 1, further including a plurality of position sensors arranged at a distal end portion of the cervical cup.

4. The uterine manipulator of claim 3, wherein the position sensors of the plurality of position sensors are arranged circumferentially around the distal end portion of the cervical cup.

5. The uterine manipulator of claim 3, wherein the position sensors of the plurality of position sensors are arranged on a distal-facing surface of the cervical cup.

6. A uterine manipulator, comprising:
   a housing;
   a shaft extending distally from the housing;
   an end effector assembly disposed at a distal end portion of the shaft, the end effector assembly including a cervical cup and a uterine manipulating tip portion extending distally from the cervical cup,
   a fluorescent tag supported by the cervical cup, the fluorescent tag configured to emit light to identify a location of the cervical cup; and
   a vibrating element supported by the cervical cup.

7. The uterine manipulator of claim 6, wherein the emitted light is non-visible to humans.

8. The uterine manipulator of claim 6, wherein the fluorescent tag is supported on a distal-facing surface of the cervical cup.

9. The uterine manipulator of claim 6, wherein the fluorescent tag is arranged circumferentially around a distal-end portion of the cervical cup.

10. The uterine manipulator of claim 6, wherein the fluorescent tag is passively fluorescent.

11. The uterine manipulator of claim 6, wherein the fluorescent tag is reactively fluorescent.

12. The uterine manipulator of claim 6, wherein the fluorescent tag includes a power source configured to activate the fluorescent tag.

13. A robotic system for operating a uterine manipulator, comprising:
   at least one robot arm configured to operate a uterine manipulator; and
   a display device configured to display images of a patient's anatomy overlaid with images of a position of the uterine manipulator relative to the patient's anatomy,
   wherein the uterine manipulator includes:
      a housing;
      a shaft extending distally from the housing;
      an end effector assembly disposed at a distal end portion of the shaft, the end effector assembly including a cervical cup and a uterine manipulating tip portion extending distally from the cervical cup; and
      a position sensor supported by the cervical cup, the position sensor configured to identify a location of the cervical cup;
      a pad including a plurality of external position sensors, the pad configured to be positioned under the patient, and the pad configured to detect a location of the position sensor supported by the cervical cup.

14. The system of claim 13, wherein the images of the patient's anatomy are CT scan images.

15. The system of claim 13, further including a surgical grasping tool supporting a second position sensor, the second position sensor configured to identify a location of the surgical grasping tool.

16. The system of claim 13, further including a position sensing scope configured to detect a position of the position sensor supported by the cervical cup.

17. The uterine manipulator of claim 13, further including at least one magnet supported by the cervical cup.

18. A uterine manipulator, comprising:
   a housing;
   a shaft extending distally from the housing;
   an end effector assembly disposed at a distal end portion of the shaft, the end effector assembly including a cervical cup and a uterine manipulating tip portion extending distally from the cervical cup;
   a position sensor supported by the cervical cup, the position sensor configured to identify a location of the cervical cup; and
   a vibrating element supported by the cervical cup, the vibrating element configured to initiate ureter peristalsis.

19. A robotic system for operating a uterine manipulator, comprising:
   at least one robot arm configured to operate a uterine manipulator;
   a display device configured to display images of a patient's anatomy overlaid with images of a position of the uterine manipulator relative to the patient's anatomy,
   wherein the uterine manipulator includes:
      a housing;
      a shaft extending distally from the housing;
      an end effector assembly disposed at a distal end portion of the shaft, the end effector assembly including a cervical cup and a uterine manipulating tip portion extending distally from the cervical cup; and
      a position sensor supported by the cervical cup, the position sensor configured to identify a location of the cervical cup; and
   a surgical grasping tool supporting a second position sensor, the second position sensor configured to identify a location of the surgical grasping tool.

20. A robotic system for operating a uterine manipulator, comprising:
   at least one robot arm configured to operate a uterine manipulator;
   a display device configured to display images of a patient's anatomy overlaid with images of a position of the uterine manipulator relative to the patient's anatomy,
   wherein the uterine manipulator includes:
      a housing;
      a shaft extending distally from the housing;
      an end effector assembly disposed at a distal end portion of the shaft, the end effector assembly including a cervical cup and a uterine manipulating tip portion extending distally from the cervical cup; and
      a position sensor supported by the cervical cup, the position sensor configured to identify a location of the cervical cup; and
   at least one magnet supported by the cervical cup.

* * * * *